United States Patent [19]
Charlesworth et al.

[11] Patent Number: 5,549,860
[45] Date of Patent: Aug. 27, 1996

[54] METHOD OF FORMING A VASCULAR PROSTHESIS

[75] Inventors: David Charlesworth, Knutsford; Christopher J. Underwood, Denton, both of Great Britain; Kerm S. Chian, Singapore, Singapore

[73] Assignee: PolyMedica Industries, Inc., United Kingdom

[21] Appl. No.: 381,297

[22] Filed: Jan. 31, 1995

Related U.S. Application Data

[63] Continuation-in-part of Ser. No. 856,223, May 13, 1992, abandoned.

[30] Foreign Application Priority Data

Oct. 18, 1989 [GB] United Kingdom .................. 8923516

[51] Int. Cl.$^6$ ............................................. B29C 41/02
[52] U.S. Cl. ............................ 264/139; 264/49; 264/154; 264/302
[58] Field of Search .......................... 264/49, 301, 302, 264/307, 154, 155, 139

[56] References Cited

U.S. PATENT DOCUMENTS

| | | | |
|---|---|---|---|
| 1,185,601 | 5/1916 | Miller | 264/301 |
| 2,086,654 | 7/1937 | Winder | 264/301 |
| 2,309,294 | 1/1943 | Auzin | 264/154 |
| 2,314,262 | 3/1943 | Winder | 264/154 |
| 2,322,858 | 6/1943 | Limbert et al. | 264/154 |
| 2,338,210 | 1/1944 | Snyder | 264/154 |
| 2,660,762 | 12/1953 | Rosenberg | 264/154 |
| 2,886,840 | 7/1959 | Hendry | 264/154 |
| 2,977,636 | 4/1961 | McGuire | 264/154 |
| 3,098,779 | 7/1963 | Cox | 264/154 |
| 3,700,380 | 10/1972 | Kitrilakis | 264/49 |
| 4,173,689 | 11/1979 | Lyman et al. | 264/41 |
| 4,311,659 | 1/1982 | Rey et al. | 264/221 |
| 4,605,406 | 8/1986 | Cahalan | 623/1 |
| 4,668,459 | 5/1987 | Joh | 264/302 |
| 4,684,490 | 8/1987 | Taller et al. | 264/301 |
| 4,707,315 | 11/1987 | Joh et al. | 264/302 |
| 4,731,073 | 3/1988 | Robinson | 623/1 |
| 4,798,607 | 1/1989 | Middleton | 623/1 |
| 4,834,747 | 5/1989 | Gogolewski | 264/41 |
| 4,857,069 | 8/1989 | Kira | 623/1 |
| 4,883,453 | 11/1989 | Berry | 600/36 |
| 4,892,544 | 1/1990 | Frisch | 264/301 |
| 4,941,870 | 7/1990 | Okada et al. | 264/49 |
| 4,957,669 | 9/1990 | Primm | 264/23 |
| 5,104,400 | 4/1992 | Berguer et al. | 264/309 |
| 5,132,066 | 7/1992 | Charlesworth | 264/184 |
| 5,137,671 | 8/1992 | Conway et al. | 264/307 |
| 5,229,045 | 7/1993 | Soldani | 264/41 |
| 5,298,276 | 3/1994 | Jayaraman | 427/2 |
| 5,462,704 | 10/1995 | Chen et al. | 264/41 |

*Primary Examiner*—Allan R. Kuhns
*Attorney, Agent, or Firm*—Dvorak and Traub

[57] ABSTRACT

A vascular prosthesis is formed from a luminate vessel by precipitating onto the vessel a sheet of polymer from a solution including an organic solvent and precipitable polymer, and forming an aperture in the sheet, the aperture communicating with the lumen of the vessel.

36 Claims, 1 Drawing Sheet

U.S. Patent    Aug. 27, 1996    5,549,860
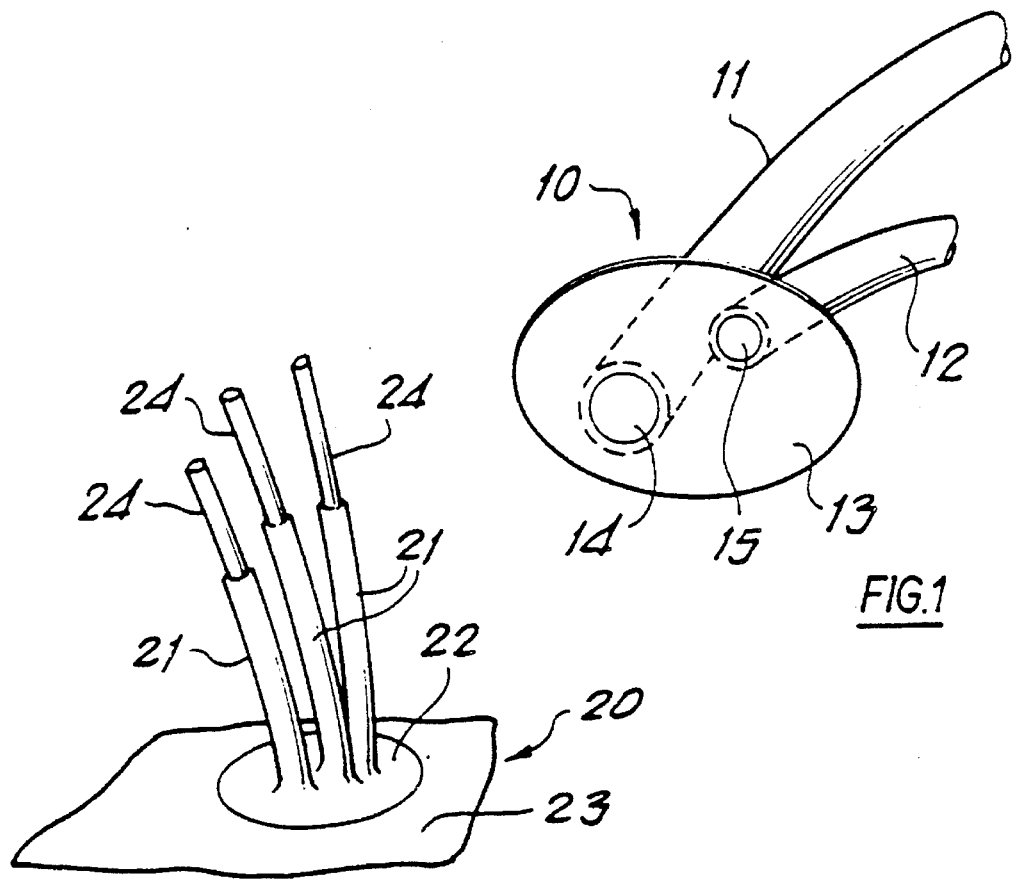
FIG.1
FIG.2
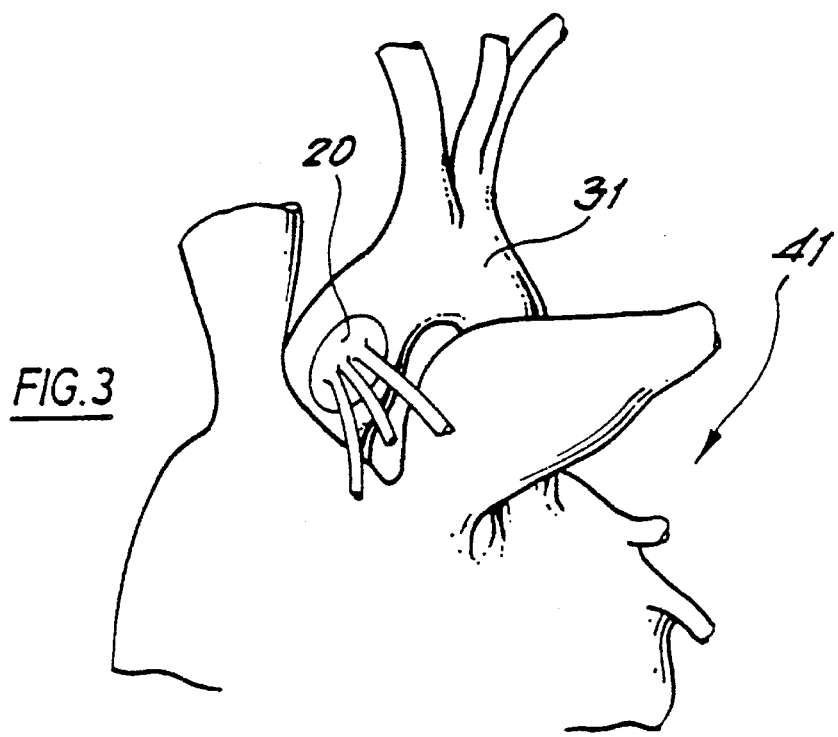
FIG.3

5,549,860

METHOD OF FORMING A VASCULAR PROSTHESIS

This application is a continuation-in-part of U.S. patent application Ser. No. 07/856,223, filed May 13, 1992, now abandoned.

BACKGROUND OF THE INVENTION

This invention relates to methods for making polymer products and to novel products made according to the methods.

Polymer products in the form of vascular prostheses conventionally comprise a conduit having varying dimensions and mechanical characteristics which are as close as materials and manufacturing processes will allow to the vessel in the body whose function it is intended that the prosthesis should replace.

A number of tubular prostheses may be grafted into a single vascular system.

There is merit, at least conceptually, in attempting to maintain as much as possible of the host vascular tissue during surgical procedures which involve vascular replacement, principally because there is less alien material introduced into the patient.

Polymer products which comprise a branch and arms emanating therefrom may typically be produced by joining the arms to an independently fabricated branch region. Whilst this procedure has the advantage that it allows the construction of relatively complex branched structures, disadvantages include the product lacking a relatively uniform mechanical consistency; together with a relatively time consuming and thus expensive preparative procedure.

Where a vascular system branches, tubular prostheses may be grafted onto each of the arms comprised thereby. This technique suffers from the serious disadvantage in that it necessitates joints at the increased number of junctions between host and prosthetic vascular material. Consequently, the time spent by the patient under anaesthetic and subject to cardiopulmonary bypass is increased which increases the likelihood of the development of pulmonary and circulatory system disorders, together with the raised possiblilty of cardiac ischaemia, necrosis and infarct.

Moreover, there is a finite possibility that a prosthesis will fail mechanically at the region of its attachment to host vascular material, conventionally regarded as the weakest and most sensitive region of the graft. An increased number of such attachment regions in a single vascular system synergistically increases the possibility of failure of the prosthetic vascular system as a whole.

SUMMARY OF THE INVENTION

The present invention provides inter alia methods of producing vascular products, particularly in the form of prostheses, which overcome the disadvantages and deficiencies which characterise prior art vascular prosthetic products.

According to the present invention there is provided a method of forming a polymer product from a luminate vessel, comprising precipitating onto said vessel a sheet of polymer from a solution comprising an organic solvent and precipitable polymer and forming an aperture in said sheet, said aperture communicating with the lumen of said vessel.

The invention further includes a method of forming a polymer product comprising a luminate vessel and sheet therearound, comprising precipitating onto a product former a layer of polymer from a solution comprising an organic solvent and precipitable polymer.

The invention also includes products made according to the aforementioned methods.

The polymer may comprise between 17 per cent and 30 per cent by weight of the solution comprising said polymer and solvent.

The product may exhibit approximately a 20 per cent shrinkage during the manufacture thereof.

The product may be formed from an existing luminate vessel, itself formed from a solution chemically similar or identical to said solution.

The polymer may be biocompatible and may comprise a vascular prosthesis.

The prosthesis may comprise a graft adapted for use in a part of a vascular system comprising branches therein, such as, for example, that part of the aorta from which the coronary arteries arise.

Said solution may further comprise a porosifier which may be insoluble in said solution but soluble in aqueous systems.

The porosifier may comprise a carbonate, such as, for example, sodium hydrogen carbonate.

Said porosifier may have an average particle size of 50 to 100 microns, and may comprise between 10 and 60 per cent by weight of the solution.

Said solution may further comprise a surfactant.

The surfactant may be an anionic detergent, such as, for example, an alkoxy sulphite.

Said surfactant may be an alkaline metal salt of dodecyl sulphate, such as sodium dodecyl sulphate.

Said surfactant may comprise between 0.1 and 10 per cent by weight of said solution.

The wall thickness of said product may be 0.5 to 1.5 millimetres, and if said product comprises a luminate vessel, the lumenal diameter thereof may be 3 to 30 mm.

The polymer of which said product is comprised may be polyurethane.

Said polyurethane may be a linear segmented poly(ether)urethane with a number average molecular weight in the region of 20 to 100 kDa.

The invention will be further apparent from the following description and several figures of the accompanying drawings, which illustrate, by way of example only, methods of forming polymer products, according to the invention and polymer products made according to the methods.

BRIEF DESCRIPTION OF THE DRAWINGS

FIG. 1 shows a method of producing a polymer vascular prosthesis from a plurality of luminate vessels;

FIG. 2 shows a second method of forming a polymer vascular prosthesis according to the invention, in which said prosthesis is precipitated onto the surface of a multi-tubular former; and FIG. 3 shows a polymer product in the form of a vascular prosthesis in situ comprising a region of the aorta from which the coronary arteries arise, together with a region of each of said arteries.

DETAILED DESCRIPTION OF THE INVENTION

FIGS. 1 and 2 illustrate methods of forming polymer products in the form of prosthetic grafts adapted for use in a region of a vascular system comprising branches therein. The precipitation process itself is known in the art, and is described in U.S. Pat. No. 4,173,689 and co-pending U.S. patent application Ser. No. 588,480, filed Sep. 26, 1990, now issued U.S. Pat. No. 5,132,066.

As shown in FIG. 1, the prosthesis 10 is formed from two luminate vessels 11, 12 by precipitating onto the open ends thereof in conjunction with a mandrel adapted for forming a sheet, a sheet 13 of polymer from a solution comprising an organic solvent and precipitable polymer. During the precipitation of the sheet onto the lumen ends, polymer may cover the open ends. Apertures 14,15 are then formed in the sheet 13, so that there is a fluid communication between the sheet 13 and the lumen of each vessel.

In a second method of forming a vascular prosthesis, the prosthesis 20 comprises a plurality of luminate vessels 21 having a sheet 22 of polymer extending radially and integrally from the vessels 21 at the open ends thereof, and is formed by precipitating onto a product former 23 or mandrel, the prothesis comprising a layer of polymer from a solution comprising an organic solvent and precipitable polymer. The product former comprises a first base portion 23 onto which the sheet 22 is formed, and a second portion 24 consisting of tubular conduits onto which the vessels 21 are formed.

FIG. 3 shows the prosthesis 20 of FIG. 2 as a graft in the aorta 31 of a human heart, shown partially at 41.

The polymer can comprise at least 17 per cent but less than 30 per cent by weight of the solution comprising said polymer and solvent and the polymer can exhibit approximately a 20 per cent shrinkage during the precipitation thereof.

Preferably, where the product is formed from an existing luminate vessel, as shown in FIG. 1, the solution from which the vessel is formed is chemically similar or identical to the solution comprising organic solvent and precipitable polymer from which solution said sheet is precipitated.

Vascular protheses necessarily should be made from biocompatible material, and the polymer of which said product is comprised is a polyurethane, characterised by being a linear segmented poly(ether)urethane with a number average molecular weight in the region of 20 to 100 kDa.

It is desirable that prostheses for use in the blood vascular system should have pores in their walls, preferably relatively large on the external surface, and relatively small on the luminal surface of the prosthesis.

Such pores enable formation of pseudointima by endothelial cells particularly, but also pericytes and other cells normally found in the vascular architecture. Such cells can present a non-thrombogenic surface to blood flowing through the prosthesis and, additionally, release factors which are ordinarily non-thrombogenic, and platelet antiaggregators and anti-thrombogenic derivatives of arachidonic acid.

In order to aid in the formation of pores in the walls of the prosthesis, the solution from which the prosthesis is precipitated preferably further comprises a porosifier, such as sodium hydrogen carbonate, which is insoluble therein but soluble, for example, in an aqueous system.

Said porosifier has an average particle size of 50 to 100 microns, and comprises between 10 and 60 per cent by weight of the solution.

A surfactant is added to the solution to modulate further the porosity of the walls, particularly at the precipitation surfaces.

Although the surfacant can comprise between 0.1 and 10 per cent by weight of said solution the preferred concentration is about 2 per cent.

The wall thickness of the prosthesis corresponds to the thicknesses of the vessels found in the body and which it is intended that the prosthesis should replace.

Alternatively, a wall thickness of the prosthesis can be determined from an analysis of the physio-mechanical requirements that must be met by the prosthesis, with relatively little regard to the wall thickness thereof.

Typically, the wall thickness of the prosthesis is 0.5 to 1.5 millimetres, and the lumenal diameter thereof is 3 to 30 mm.

Although the present invention has been described in conjunction with particular embodiments, it will be appreciated by those skilled in the art than various other changes, omissions and additions thereto may be made without departing from its scope as described herein.

For example, the polymer products may comprise biocompatible sheets having pores, the sheets acting as matrices into which cells may migrate in tissue culture. Such sheets may be of use in skin grafts, for example.

The polymer products may be used as filters and selectively permeable membranes.

We claim:

1. A method for forming a polymeric vascular prosthesis from a polymeric vessel having a lumen open at one end, the steps comprising precipitating from a solution onto said one end of said vessel a sheet of polymer extending radially and integrally therefrom; and forming an aperture in said sheet at the position of said lumen so as to allow fluid communication with the lumen at said one end of the vessel.

2. The method according to claim 1, wherein the polymer comprises at least 17 per cent but less than 30 per cent by weight of the solution comprising said polymer and solvent.

3. The method according to claim 2, wherein during formation of said prosthesis, there is approximately a 20 percent shrinkage of the part of the prosthesis being formed.

4. The method according to claim 1, wherein the polymer is chemically similar or identical to the material from which the polymeric vessel is made.

5. The method according claim 1, wherein the polymer is bio-compatible.

6. The method according to claim 1, wherein said solution further comprises a porosifier.

7. The method according to claim 6, wherein said porosifier is insoluble in said solution.

8. The method according to claim 7, wherein the porosifier is soluble in aqueous systems.

9. The method according to claim 6, wherein the porosifier comprises a carbonate.

10. The method according to claim 9, wherein the porosifier is sodium hydrogen carbonate.

11. The method according to claim 6, wherein the porosifier has an average particle size of 50 to 100 microns.

12. The method according to claim 6, wherein the porosifier comprises between 10 and 60 per cent by weight of the solution.

13. The method according to claim 1, wherein said solution further comprises a surfactant.

14. The method according to claim 13, wherein the surfactant is an anionic detergent.

15. The method according to claim 14, wherein the anionic detergent is an alkoxy sulphite.

16. The method according to claim 13, wherein the surfactant is an alkaline metal salt of dodecyl sulphate.

17. The method according to claim 13, wherein the surfactant is sodium dodecyl sulphate.

18. The method according to claim 13, wherein the surfactant comprises between 0.1 and 10 per cent by weight of said solution.

19. The method according to claim 1, wherein said product has a wall and said wall has a thickness of 0.5 to 1.5 millimeters.

20. The method according to claim 1, wherein said lumen has a diameter of 3 to 30 mm.

21. The method according to claim 1, wherein the polymer comprises polyurethane.

22. The method according to claim 21, wherein the polyurethane is a linear segmented poly(ether)urethane with a number average molecular weight in the region of 20 to 100 kDa.

23. The method according to claim 1, wherein the solvent comprises N,N-Dimethylacetamide.

24. The method according to claim 1, wherein the prosthesis comprises a graft adapted for use in a part of a vascular system comprising branches therein.

25. The method according to claim 24, wherein the prosthesis comprises a graft adapted to replace that part of the aorta from which the coronary arteries exit.

26. A method for forming a polymeric vascular prosthesis comprising a vessel having a lumen open at one end and a sheet extending radially and integrally from the vessel at said one end, comprising the steps of
   precipitating a layer of polymer from a solution comprising an organic solvent and precipitable polymer onto a prosthesis form, said prosthesis form comprising a first portion onto which the sheet is precipitated and a second portion onto which the vessel is precipitated, and
   separating the formed prosthesis from the product form.

27. The method of claim 26, wherein the prosthesis has a plurality of vessels and the prosthesis form has a corresponding number of second portions.

28. The method according to claim 26, wherein the polymer comprises at least 17 per cent but less than 30 per cent by weight of the solution comprising said polymer and solvent.

29. The method according claim 26, wherein the polymer is bio-compatible.

30. The method according to claim 26, wherein said product has a wall and said wall has a thickness of 0.5 to 1.5 millimeters.

31. The method according to claim 26, wherein said lumen has a diameter of 3 to 30 mm.

32. The method according to claim 26, wherein the polymer comprises polyurethane.

33. The method according to claim 32, wherein the polyurethane is a linear segmented poly(ether)urethane with a number average molecular weight in the region of 20 to 100 kDa.

34. The method according to claim 26, wherein the solvent comprises N,N-Dimethylacetamide.

35. The method according to claim 26, wherein the prosthesis comprises a graft adapted for use in a part of a vascular system comprising branches therein.

36. The method according to claim 35, wherein the prosthesis comprises a graft adapted to replace that part of the aorta from which the coronary arteries exit.

* * * * *